(12) United States Patent
Srinivasan

(10) Patent No.: US 10,206,742 B2
(45) Date of Patent: Feb. 19, 2019

(54) FIBER EMBEDDED HOLLOW SPIKES FOR PERCUTANEOUS DELIVERY OF LASER ENERGY

(71) Applicant: C Laser, Inc., Lebanon, IN (US)

(72) Inventor: Pattanam Srinivasan, Lebanon, IN (US)

(73) Assignee: C Laser, Inc., Lebanon, IN (US)

( * ) Notice: Subject to any disclaimer, the term of this patent is extended or adjusted under 35 U.S.C. 154(b) by 1187 days.

(21) Appl. No.: 14/254,129

(22) Filed: Apr. 16, 2014

(65) Prior Publication Data

US 2014/0243806 A1 Aug. 28, 2014

Related U.S. Application Data

(63) Continuation-in-part of application No. 13/022,178, filed on Feb. 7, 2011, now Pat. No. 9,693,825, which
(Continued)

(51) Int. Cl.
*A61B 18/18* (2006.01)
*A61B 18/20* (2006.01)
(Continued)

(52) U.S. Cl.
CPC .......... *A61B 18/201* (2013.01); *A61N 5/0601* (2013.01); *A61B 2018/00434* (2013.01); *A61B 2018/00577* (2013.01); *A61B 2018/2005* (2013.01); *A61B 2018/2227* (2013.01); *A61N 2005/063* (2013.01); *A61N 2005/0612* (2013.01); *A61N 2005/0662* (2013.01)

(58) Field of Classification Search
CPC .................................................. A61N 5/0601
See application file for complete search history.

(56) References Cited

U.S. PATENT DOCUMENTS 4,566,438 A * 1/1986 Liese ................... A61B 5/0084
600/129
4,959,063 A * 9/1990 Kojima ................. A61B 18/24
604/44
(Continued)

FOREIGN PATENT DOCUMENTS

DE 44 29 192 2/1996
DE 200 03 349 6/2000
(Continued)

OTHER PUBLICATIONS

European Search Report issued in Application No. 11858224.6 dated Feb. 27, 2015, 3 pages.
(Continued)

*Primary Examiner* — John R Downey
(74) *Attorney, Agent, or Firm* — Fish & Richardson P.C.

(57) ABSTRACT

Some implementations provide an apparatus for percutaneous delivery of laser energy, the apparatus including two or more hollow spikes, each having an insertion end and a coupling end, each including an optical fiber embedded as a permanent fixture therein, each optical fiber capable of emitting laser from the insertion end of the corresponding hollow spike; and\a hub coupled to the two or more hollow spikes at the respective coupling ends of each hollow spike, the hub including a connector for coupling the apparatus to a laser generator.

17 Claims, 21 Drawing Sheets

Related U.S. Application Data is a continuation-in-part of application No. 12/631,835, filed on Jan. 8, 2010, now Pat. No. 9,149,647.

(51) Int. Cl.

| A61N 5/06 | (2006.01) |
|---|---|
| A61B 18/22 | (2006.01) |
| A61B 18/00 | (2006.01) |

(56) References Cited

U.S. PATENT DOCUMENTS

| 5,464,436 | A | 11/1995 | Smith |
| 5,514,126 | A | 5/1996 | Prescott |
| 5,772,597 | A * | 6/1998 | Goldberger .......... A61B 5/0084 |
| | | | 600/473 |
| 5,807,261 | A | 9/1998 | Benaron et al. |
| 6,080,148 | A | 6/2000 | Damasco et al. |
| 6,152,918 | A * | 11/2000 | Padilla .............. A61B 17/3403 |
| | | | 606/15 |
| 6,157,854 | A | 12/2000 | Haber |
| 6,224,566 | B1 * | 5/2001 | Loeb ................. A61M 25/0084 |
| | | | 604/20 |
| 6,267,779 | B1 | 7/2001 | Gerdes |
| 6,519,485 | B2 | 2/2003 | Wiesmann et al. |
| 6,663,659 | B2 | 12/2003 | McDaniel |
| 6,921,413 | B2 | 7/2005 | Mahadevan-Jansen et al. |
| 6,942,658 | B1 | 9/2005 | Rizoiu et al. |
| 7,976,571 | B2 | 7/2011 | Neuberger |
| 2001/0056278 | A1 | 12/2001 | Nield et al. |
| 2002/0045922 | A1 | 4/2002 | Nield et al. |
| 2002/0182186 | A1 * | 12/2002 | Loeb .................... A61F 9/0008 |
| | | | 424/93.7 |
| 2003/0028147 | A1 | 2/2003 | Ayes et al. |
| 2003/0120267 | A1 | 6/2003 | Kaufman et al. |
| 2003/0212388 | A1 | 11/2003 | Ronn |
| 2003/0225331 | A1 | 12/2003 | Diederich et al. |
| 2004/0014199 | A1 | 1/2004 | Streeter |
| 2004/0082942 | A1 | 4/2004 | Katzman |
| 2004/0111132 | A1 | 6/2004 | Shenderova |
| 2005/0049582 | A1 | 3/2005 | DeBenedictis et al. |
| 2005/0065577 | A1 | 3/2005 | McArthur et al. |
| 2005/0113658 | A1 * | 5/2005 | Jacobson ........... A61B 5/14532 |
| | | | 600/342 |
| 2005/0182293 | A1 | 8/2005 | Katzman |
| 2005/0283148 | A1 | 12/2005 | Janssen et al. |
| 2006/0122535 | A1 * | 6/2006 | Daum .................... A61B 10/02 |
| | | | 600/565 |
| 2006/0206172 | A1 | 9/2006 | DiMauro |
| 2007/0162093 | A1 | 7/2007 | Porter |
| 2007/0179485 | A1 | 8/2007 | Yeik et al. |
| 2007/0185367 | A1 | 8/2007 | Abdou |
| 2007/0213792 | A1 | 9/2007 | Yaroslaysky |
| 2008/0027520 | A1 * | 1/2008 | Choi .................. A61B 17/1688 |
| | | | 607/89 |
| 2008/0077198 | A1 | 3/2008 | Webb et al. |
| 2008/0091249 | A1 | 4/2008 | Wang |
| 2008/0125836 | A1 | 5/2008 | Streeter et al. |
| 2008/0140023 | A1 | 6/2008 | McMillan |
| 2008/0249517 | A1 * | 10/2008 | Svanberg ............. A61N 5/0601 |
| | | | 606/15 |
| 2009/0069673 | A1 | 3/2009 | Tapalian et al. |
| 2009/0124958 | A1 * | 5/2009 | Li ........................ A61B 18/203 |
| | | | 604/20 |
| 2009/0125036 | A1 | 5/2009 | Bleich |
| 2009/0299349 | A1 | 12/2009 | Kubota et al. |
| 2010/0016783 | A1 | 1/2010 | Bourke et al. |
| 2010/0152715 | A1 * | 6/2010 | Srinivasan ........... A61N 5/0601 |
| | | | 606/3 |
| 2011/0196357 | A1 * | 8/2011 | Srinivasan ........... A61B 18/201 |
| | | | 606/15 |
| 2011/0218524 | A1 | 9/2011 | Catlaneo |
| 2011/0301581 | A1 | 12/2011 | Thyzel |
| 2012/0089135 | A1 | 4/2012 | Srinivasan |
| 2013/0281839 | A1 | 10/2013 | Jain et al. |
| 2013/0324989 | A1 * | 12/2013 | Leung .................... A61B 18/02 |
| | | | 606/24 |
| 2014/0243806 | A1 * | 8/2014 | Srinivasan ........... A61B 18/201 |
| | | | 606/15 |
| 2016/0015997 | A1 | 1/2016 | Srinivasan |

FOREIGN PATENT DOCUMENTS

| JP | 2009207605 A | 9/2009 |
| KR | 100 963 395 | 6/2010 |
| WO | WO 1998/033557 | 8/1998 |
| WO | WO2000057804 A1 | 10/2000 |
| WO | WO 2001/062171 | 8/2001 |

OTHER PUBLICATIONS

U.S. Final Office Action for U.S. Appl. No. 12/631,835 dated Jan. 12, 2015, 23 pages.
U.S. Notice of Allowance in U.S. Appl. No. 13/329,596, dated Dec. 24, 2014, 14 pages.
Communication Pursuant to Article 94(3) EPC issued in EP 11858224.6 dated Mar. 19, 2015, 5 pages.
Communication Pursuant to Article 94(3) EPC issued in EP 11858106.5, dated Nov. 10, 2015, 3 pages.
U.S. Final Office Action for U.S. Appl. No. 13/022,178 dated Sep. 24, 2015, 13 pages.
U.S. Notice of Allowance in U.S. Appl. No. 14/727,140, dated Oct. 26, 2015, 18 pages.
International Preliminary Report on Patentability for PCT/US2015/025870, dated Oct. 27, 2016, 8 pages.
U.S. Non-Final Office action for U.S. Appl. No. 14/870,327, dated Oct. 6, 2016, 12 pages.
U.S. Final Office action for U.S. Appl. No. 13/022,178 dated Aug. 25, 2016, 15 pages.
"Local Anesthetic," Wikipedia, the free encyclopedia, downloaded from the Internet on Nov. 27, 2012, 10 pages http://en.wikipedia.org/wiki/Local_anesthetic.
Morgan & Mikhail, Clinical Anesthesiology, second edition, Chapter 18, Pain Management, pp. 274-280 (12 total pages).
Schenk et al.; Percutaneous Laser Disk Decompression: A Review of Literature; AJNR 27; Jan. 2006; www.ajnr.org.
Singh et al.; Percutaneous Lumbar Laser Disc Decompression: A Systematic Review of Current Evidence; Pain Physician 2009; 12:573-588 ISSB 1533-3159; www.painphysicianjournal.com.
Tsai et al.; Plasma-mediated ablation: an optical tool for submicrometer surgery on neuronal and vascular systems; Science Direct, Current Opinion in Biotechnology 2009, 20:1-10; www.sciencedirect.com.
Turgut et al.; Extensive Damage to the End-Plates as a Complication of Laser Discectomy An Experimental Study Using an Animal Model; Acta Neurochirurgical 1997; 139: 404-410.
PCT Notification of Transmittal of the International Search Report and the Written Opinion of the International Searching Authority, or the Declaration issued in PCT/US2011/064376 dated Feb. 6, 2012, 7 pages.
PCT International Preliminary Report on Patentability for Application No. PCT/US2011/064376 dated Aug. 13, 2013, 7 pages.
PCT Notification of Transmittal of the International Search Report and the Written Opinion of the International Searching Authority, or the Declaration issued in PCT/US2011/066006 dated Apr. 19, 2012, 7 pages.
PCT International Preliminary Report on Patentability for Application No. PCT/US2011/066006 dated Aug. 13, 2013, 7 pages.
European Office Action in Application No. 11858106.5, dated Sep. 2, 2014, 5 pages.
European Search Report in Application No. 11858106.5, dated Aug. 21, 2014, 3 pages.
U.S. Non-Final Office Action for U.S. Appl. No. 12/631,835 dated Dec. 20, 2011, 12 pages.
U.S. Final Office Action for U.S. Appl. No. 12/631,835 dated Jun. 19, 2012, 19 pages.
U.S. Non-Final Office Action for U.S. Appl. No. 12/631,835 dated Sep. 4, 2012, 26 pages.

(56) References Cited

OTHER PUBLICATIONS

U.S. Final Office Action for U.S. Appl. No. 12/631,835 dated Mar. 14, 2013, 31 pages.
U.S. Non-Final Office Action for U.S. Appl. No. 12/631,835 dated Mar. 14, 2014, 30 pages.
U.S. Non-Final Office Action for U.S. Appl. No. 13/022,178 dated Dec. 20, 2011, 11 pages.
U.S. Non-Final Office Action for U.S. Appl. No. 13/022,178 dated Aug. 17, 2012, 13 pages.
U.S. Final Office Action for U.S. Appl. No. 13/022,178 dated Feb. 13, 2013, 14 pages.
U.S. Non-Final Office Action for U.S. Appl. No. 13/022,178 dated Jan. 30, 2014, 18 pages.
U.S. Final Office Action for U.S. Appl. No. 13/022,178 dated Jul. 17, 2014, 15 pages.
U.S. Non-Final Office Action for U.S. Appl. No. 13/329,596 dated Nov. 14, 2013, 16 pages.
U.S. Notice of Allowance in U.S. Appl. No. 13/329,596, dated Sep. 23, 2014, 10 pages.
U.S. Non-Final Office Action for U.S. Appl. No. 13/022,178 dated Apr. 23, 2015, 19 pages.
U.S. Notice of Allowance in U.S. Appl. No. 12/631,835 , dated Jul. 9, 2015, 17 pages.
International Search Report and Written Opinion in International Application No. PCT/US2015/025870, dated Jul. 24, 2015, 9 pages.

\* cited by examiner

FIBER EMBEDDED HOLLOW SPIKES FOR PERCUTANEOUS DELIVERY OF LASER ENERGY

CROSS-REFERENCE TO RELATED APPLICATIONS

This application is a continuation-in-Part of U.S. application Ser. No. 13/022,178, filed Feb. 7, 2011, which is a continuation-in-part of U.S. application Ser. No. 12/631, 835, filed Jan. 8, 2010, which claims benefit of U.S. Provisional Patent Application No. 61/122,393, filed Dec. 14, 2008, the entirety of each of which are incorporated by reference herein.

BACKGROUND

Laser energy can be delivered to biologic tissue for medical use.

SUMMARY

In one aspect, some implementations provide an apparatus for percutaneous delivery of laser energy, the apparatus including: two or more hollow spikes, each having an insertion end and a coupling end, each including an optical fiber embedded as a permanent fixture therein, each optical fiber capable of emitting laser from the insertion end of the corresponding hollow spike; and a hub coupled to the two or more hollow spikes at the respective coupling ends of each hollow spike, the hub including a connector for coupling the apparatus to a laser generator.

Implementations may include one or more of the following features. The insertion end may include a cutting edge. The respective optical fiber may be embedded such that the respective optical fiber may be housed in the insertion end of the corresponding hollow spike but the respective optical fiber may not protrude into the cutting edge of the insertion end. The embedded optical fiber may be permanently fixed within the respective spike with glue. The glue includes a bioadhesive. The respective spike has an outer diameter of 0.7 mm or less. The embedded optical fiber may be affixed within the insertion end of the respective spike to deliver the laser energy to an area of treatment on contact with the cutting edge, and wherein the embedded optical fiber may be affixed within the insertion end to prevent splitting and damage to the optical fiber. The cutting edge may include a beveled edge.

The apparatus may further include at least one laser generator that generates a laser of a wavelength in the 690 nm to 710 nm range. The respective optical fiber may have a diameter that is less than one of 0.7 mm or 0.5 mm. Each hollow spike may be spaced no more than 1 cm away from at least one neighboring spike. The respective optical fiber may include a multi-mode fiber. Each hollow spike may include a Quincke type spinal needle.

The apparatus may further include: an imaging device to track the insertion ends of the two or more hollow spikes. The imaging device may include an X-Ray fluoroscopy device. The imaging device may include: an ultrasound device. The apparatus may include a motor connected to the hub, the motor configured to cause the percutaneous delivery of laser energy to change position inside a treatment area.

In another aspect, some implementations provide A method of percutaneous application of laser energy for medical treatment, the method including: coupling a laser generator to a hub that is connected to two or more hollow spikes, wherein a connector included in the hub is configured to couple the laser generator the hub, and wherein each hollow spike includes a beveled edge distal from a portion of the spike connected to the hub, each hollow spike housing an optical fiber; percutaneously inserting the beveled edges of the two or more hollow spikes into a treatment area through a subject's skin, wherein the two or more hollow spikes are inserted at a same time; and delivering laser energy to the treatment area through the optical fibers housed within the two or more spikes.

Implementations may include one or more of the following features. Percutaneously inserting the beveled edges may include inserting the beveled edges under imaging guidance. Delivering the laser energy may include: targeting laser energy within the treatment area under imaging guidance.

The details of one or more aspects of the subject matter described in this specification are set forth in the accompanying drawings and the description below. Other features, aspects, and advantages of the subject matter will become apparent from the description, the drawings, and the claims.

DESCRIPTION OF DRAWINGS

The figures are for illustration purposes only and are not necessarily drawn to scale. The invention itself, however, may best be understood by reference to the detailed description which follows when taken in conjunction with the accompanying drawings in which.

Like reference symbols in the various drawings indicate like elements.

DETAILED DESCRIPTION

Figure 1:
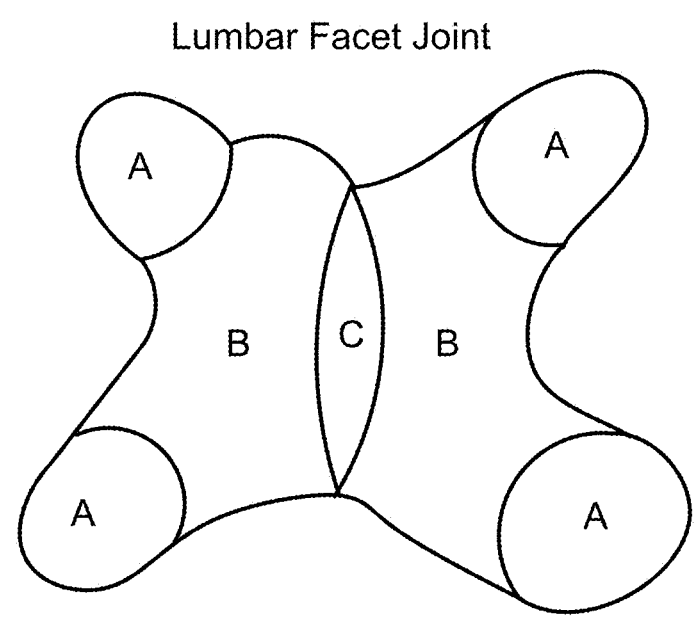
FIG. 1 is a diagram representative of an anterior-posterior (AP) AP X-Ray view of lumbar facet joints.

In some implementations, a spinal needle may be incorporated for laser delivery deep into the body. In one configuration, the laser fiber is fixed within the spinal needle as one unit using a Luer lock mechanism to prevent movement.

In particular, in deep tissue low intensity laser therapy (DT-LILT), a low intensity laser capable of producing cell resonance within the nerve cell can selectively cause destruction of the nerve cells without affecting the surrounding tissues. The selection of laser wavelength generally depends on the absorption characteristics of the nerve cells. Heat may be generated, but is not particularly necessary as the selective destruction of the nerve cells takes place by cell resonance rather than heat coagulation. This technique is referred to herein as deep tissue low intensity laser neuroablation (DT-LILNA) and is different from other medical or tissue lasers whose primary effect is through heat generation.

A delivery system for DT-LILT includes a laser generator capable of generating the appropriate wavelength. In some implementations, the wavelengths used are in the 690 nanometers (nm) to 710 nm range. The laser fibers used in the performing the process may have diameters that are less than 0.7 millimeters (mm), or less than 0.5 mm.

The above-described laser treatment preferably uses a common Quincke spinal needle with the laser fiber fixated in the needle. In one configuration, laser fiber may be fixed using a Luer lock mechanism with the Quincke needle. Such fixation can also be achieved by making the laser fiber and the spinal needle as one non detachable unit, as will be discussed in more detail below.

Preferred laser characteristics may include:

1. Laser Wavelength: 700 nm to 705 nm
2. Laser Output Average Power: 4 milliwatts (mW) to 6 mW (range 1 mW to 6 mW)
3. Laser Pulsation, pulsed at nanoseconds or picoseconds.
4. Laser is Timer controlled: between about 5 seconds and about 10 seconds.

In some implementations, the laser may be pulsed at 25 nanoseconds, with an output peak power of 40 nanowatts (nW) (+/−8 nW). In some implementations, the diameter of the laser fiber may range between 200 microns and 300 microns.

The intra-operative treatment methodology may include applying the laser treatment based on the above described laser characteristics to facet joint neuroablation (also synonymous with medial branch neuroablation). Conventional neuroablation may depend on locating the medial branch nerve in an oblique/lateral X ray view and using heat or chemical substance to destroy the medial branch. The method described herein may permit the use of a simple anterior-posterior (AP) X-ray view and obtain correct positioning for deep tissue low intensity laser neuroablation (DT-LILNA).

The laser treatment points applied to a joint during a DT-LILT treatment session according to some implementations are described next. The example DT-LILT treatment session is provided in the context of treating the lumbar facet joint. However, the use of the laser for therapeutic treatment is not limited to these points, and these laser points can be applicable to all facet joints, including thoracic and cervical facet joints. When the size of the facet joint is smaller, the laser points and the laser area may be reduced but the pattern of laser delivery remains substantially the same.

FIG. 1 is a diagram representative of an AP X-Ray view of Lumbar Facet Joints. As shown in FIG. 1, area A is the Facet Joint (also known as pars articularis), area B is the Lamina, and area C is the Spinous Process. The example laser points that may be delivered in some implementations are illustrated next with reference to FIGS. 2-8.

Figure 2:
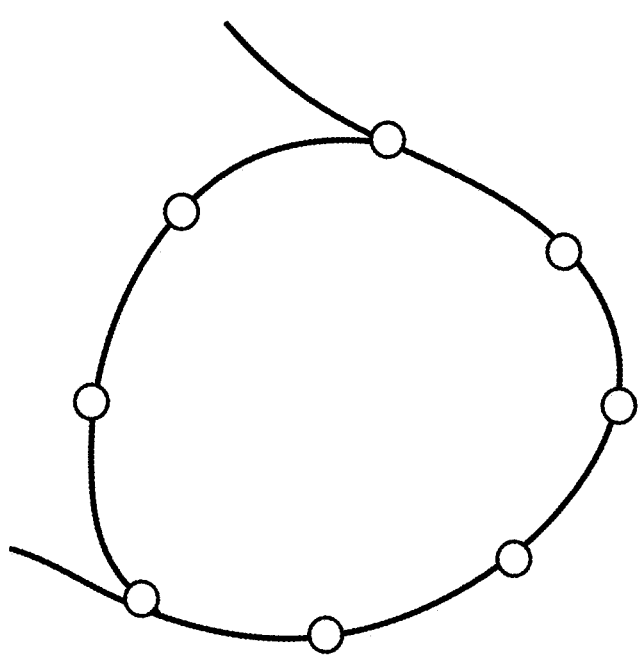
FIG. 2 is a diagram illustrating an example technique in which laser points are used in a single lumbar facet joint using 8 points in a circular fashion around the facet joint.
Figure 3:
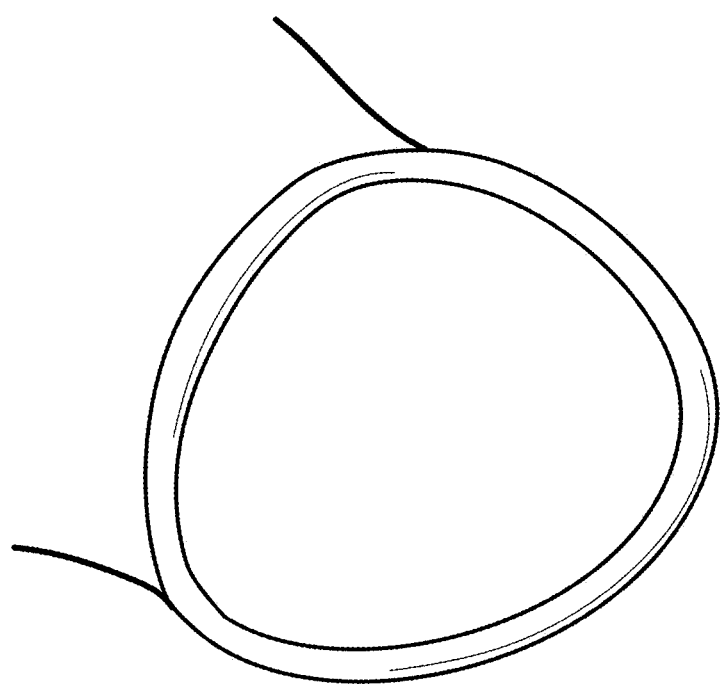
FIG. 3 is a diagram illustrating an example technique in which laser points are applied in continuous circular fashion around the facet joint.

FIG. 2 shows a technique in which the Laser points are used in a single lumbar facet using 8 points in a circular fashion around the facet joint. For example, the laser may be delivered by applying the illustrated eight discrete treatment points serially along the circular path. Another technique is illustrated in FIG. 3, in which the laser is applied in a continuous circular fashion around the facet joint. For example, the laser delivery may be driven by a motorized device to scan the illustrated circle. The motorized device may include a step motor, or a circular motor. The motor may be a programmed motor. In some implementations, the laser delivery may be manual. For example, a medical doctor may deliver laser treatment as if drawing a circle on a canvas. This technique may also be used to identify areas of laser delivery and treatment remotely, using robotic arms when a professional using the laser device is located elsewhere.

Figure 4:
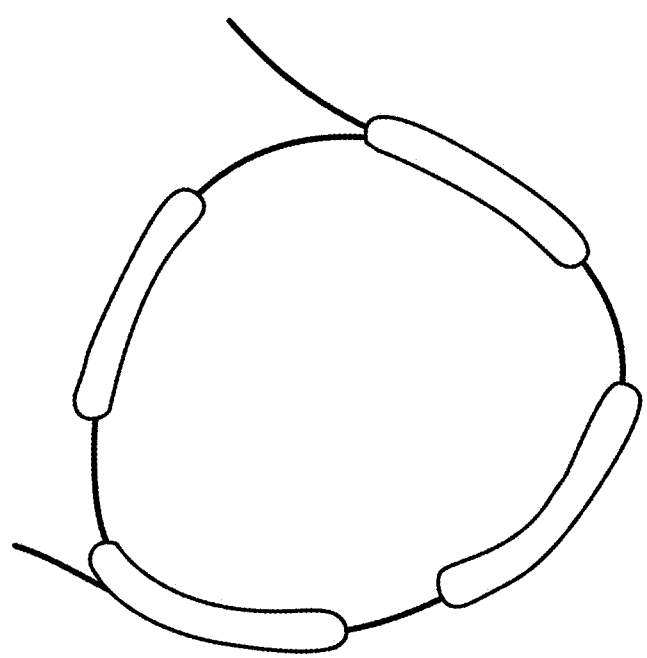
FIG. 4 is a diagram illustrating an example technique in which laser points are applied in 4 semi continuous patterns around the facet joint.

FIG. 4 illustrates another example technique in which four semi-continuous patterns are used around the facet joint. The delivery may be motorized or manual, as described herein.

Figure 5:
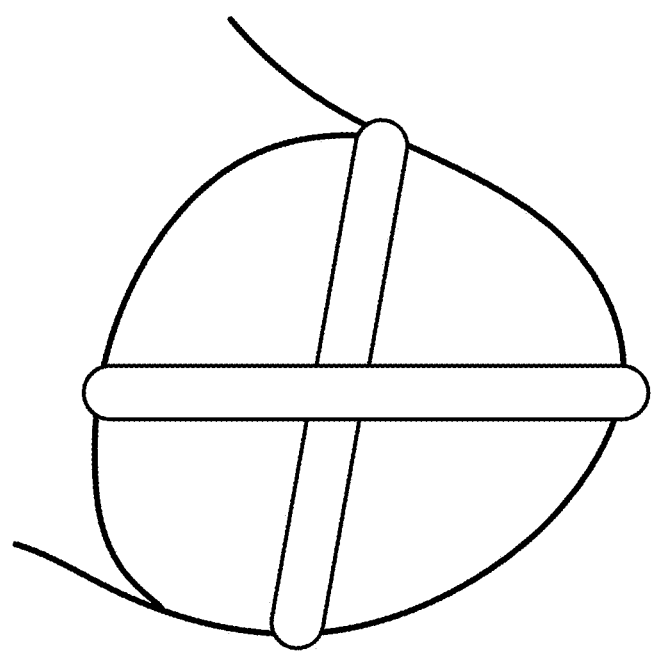
FIG. 5 is a diagram illustrating an example technique in which laser points on a single lumbar facet joint use a continuous cross pattern across the facet joint.
Figure 6:
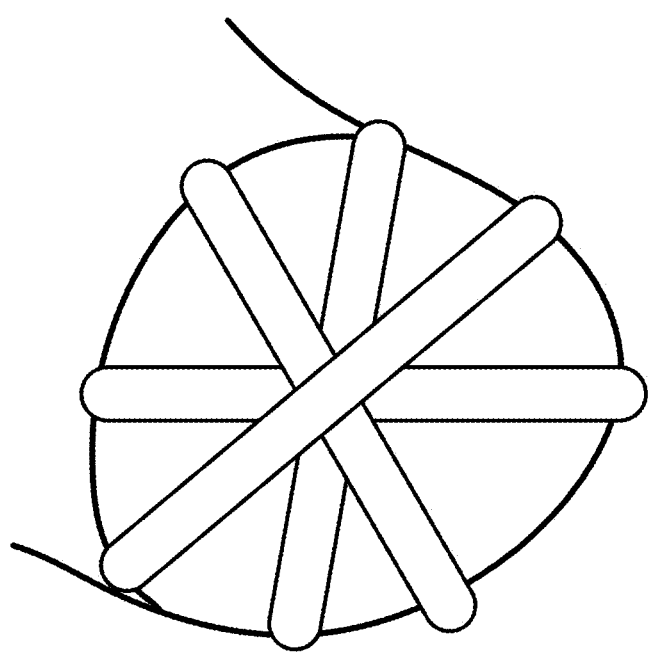
FIG. 6 is a diagram illustrating an example technique in which laser points on a single lumbar facet use continuous multiple cross patterns across the facet joint.
Figure 7:
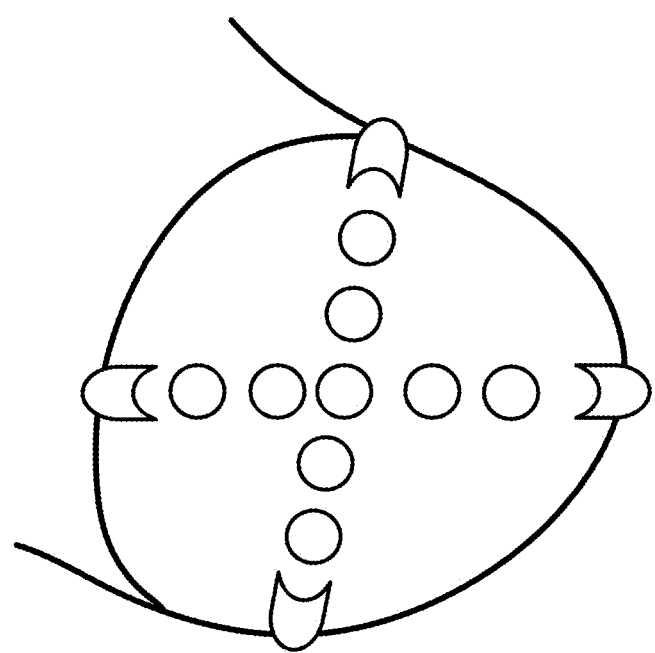
FIG. 7 is a diagram illustrating an example technique in which laser points on a single lumbar facet use a continuous intermittent pattern 4 across the facet joint.
Figure 8:
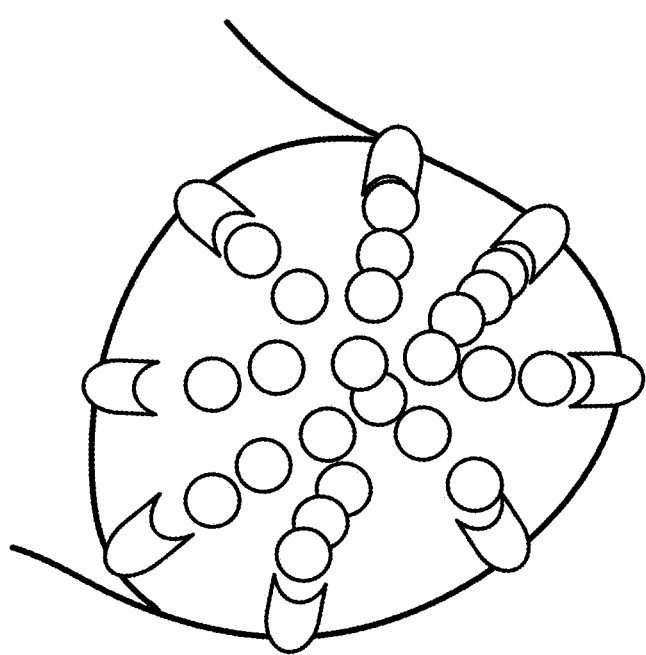
FIG. 8 is a diagram illustrating a technique in which laser points on a single lumbar facet use a continuous intermittent pattern multiple times across the facet joint.

FIG. 5 illustrates the delivered laser points on a single lumbar facet joint according to some implementations. The laser points follow another pattern: a continuous cross fashion across the facet joint. FIG. 6 shows the laser points using continuous multiple cross fashion across the facet joint, forming a pattern of spokes, in corresponding with the outer diameter is facet joint under AP view X-Ray FIG. 7 shows application of the laser on a cross pattern where the laser delivery points are discrete dots across the facet joint. This technique may be referred to as the continuous intermittent approach. FIG. 8 shows application of the laser in a continuous intermittent fashion multiple times across the facet joint to form a pattern of spokes.

The delivery of laser energy deep into the body for therapeutic use through the percutaneous method using an initial hollow probe or hollow needle placement can be cumbersome especially when the diameter of the hollow is small and the laser fiber that is to be inserted is even smaller.

Moreover, even when the laser fiber is secured by use of a Luer lock, the placement of the laser fiber may still be insecure. In particular, when using a Luer lock, inserting the fiber within the spinal needle and affixing the fiber with a Luer lock mechanism may be prone to user errors, despite careful visualization of the tip of the spinal needle to prevent protrusion of the laser fiber beyond the needle tip. Even if such protrusion is minimal, the protrusion can cause pain and discomfort in the patient during percutaneous insertion. Hollow or spinal needles inserted with protruded tips may also split or damage the laser fiber, resulting in improper laser delivery to the area intended for treatment.

Moreover, first inserting the hollow probe or the hollow needle or a spinal needle and then subsequently inserting the laser fiber could result in migration of the laser fiber beyond the needle tip. When migration takes place, precision for the area of intended treatment may be lost. This is because the needle tip is already embedded in the human body and is no longer under visual control. Such migration is contraindicated in spinal procedures where precision is desired. Repositioning the needle under these circumstances can also lead to unrecognized or unintended migration of the laser fiber. Furthermore, migration of the laser fiber during laser delivery can irritate or even damage the healthy tissues not in need of treatment.

As described above, deep tissue laser treatments may be facilitated using a hollow needle and a laser fiber that passes through that hollow needle. However free movement of the laser fiber within the hollow needle may not be safe and can result in the laser fiber getting in the way of needle movement. Free laser fiber movement within the hollow needle may also result in laser fiber damage by the needle tip resulting in improper and imprecise laser energy delivery within the human body. These problems can be avoided by permanently embedding the laser fiber within the hollow needle and making the hollow needle and the laser fiber as one non-detachable unit. Such an arrangement can effectively prevent movement of the laser fiber within the hollow needle. The following describes in detail how the laser fiber may be embedded in a cutting edge hollow needle, such as a Quincke type spinal needle, so that the laser energy may be delivered in a safe and precise manner deep into the body.

Taking the above into consideration, an implementation of the needle and fiber, in which the fiber is embedded in the hollow needle is described herein, in which the hollow needle and the laser fiber are formed as one non-detachable unit. This configuration offers excellent advantages and safety during delivery of laser energy over the other hollow probe or hollow needle or spinal needle/laser fiber combinations. This technique, described in detail as follows, allows for easy insertion and precise delivery of laser energy to the area intended for treatment in a safe manner.

Figure 9:
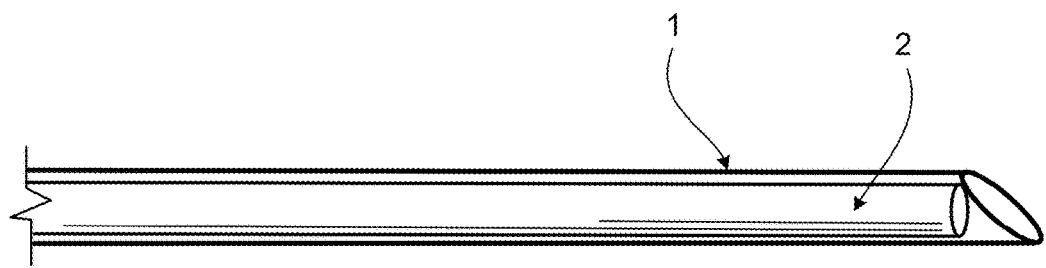
FIG. 9 a diagram that shows an example hollow needle and permanently embedded laser fiber in accordance with an embodiment of the present application.
Figure 10:
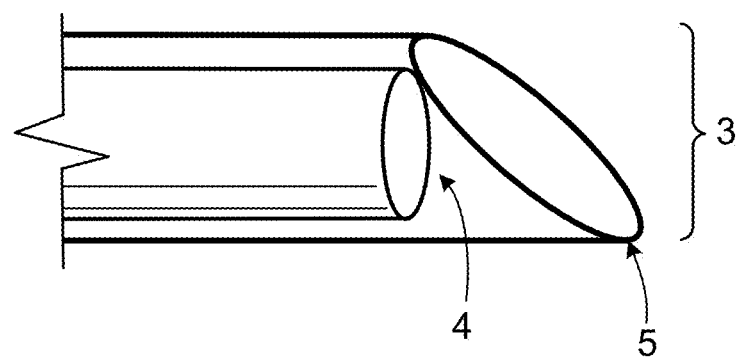
FIG. 10 is a diagram showing details of the tip of an example hollow needle used for delivering laser energy to a facet joint.
Figure 11:
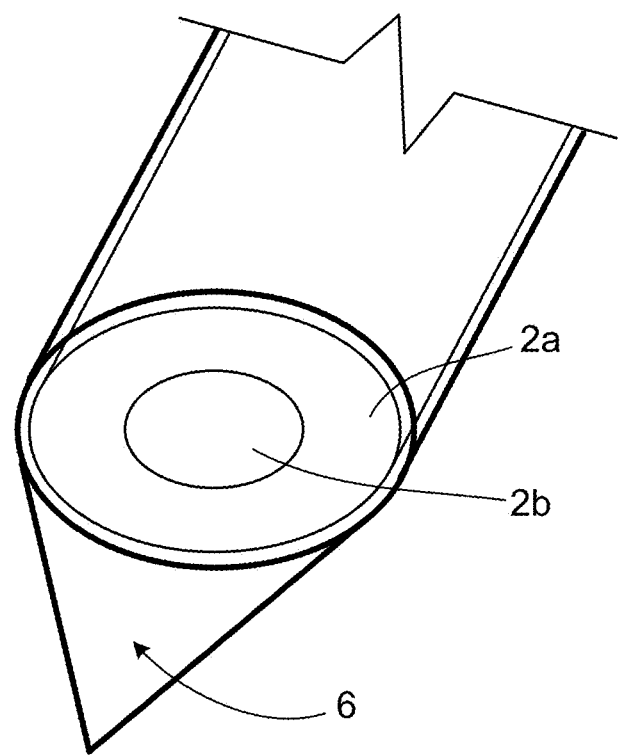
FIG. 11 is an alternate view of the example needle used for delivering laser energy to a facet joint.

An example embodiment of such a needle and laser fiber is shown in FIGS. 9-11. FIG. 9 shows the hollow needle 1 and the permanently embedded laser fiber 2 provided therein. The laser fiber may include a multi-mode fiber having an inner core and an outside cladding. The inner core may be typically 50-100 micrometers in diameter. The outer core may amount to a diameter of 200-300 micrometer. In some implementations, the laser area of the tissue under treatment may be confined to the laser fiber diameter with less than 1 cm scatter.

FIG. 10 shows the tip of the hollow needle along with the embedded laser fiber in magnification. The external diameter 3 of the hollow needle may vary from 0.7 mm or 22 G to 0.5 mm or 25 G. The tip of the needle 1 includes sharp edge of the bevel 5 that enables the hollow needle to pierce, and is characteristic of Quincke type spinal needles, also known as cutting edge spinal needles.

The tip of embedded laser fiber 4 is positioned to stop short of the tapering cutting edge of the hollow needle, as illustrated. In FIG. 11, the hollow needle is viewed from above. In this view it can be seen that the tip of the embedded laser fiber 2 is clear of the tapering cutting edge, leaving a triangular space 6 between the cutting edge of the hollow needle 1 and the tip of the embedded laser fiber 2. To maintain the fiber 2 in this preferred condition, the fiber 2 is affixed permanently within the hollow needle 1. Laser may be delivered through the core of the fiber, which includes the cavity 2a. The cladding or fiber covering 2b may provide structure shielding. The laser fiber is fixed to the inner wall of the Quincke spinal needle with a bioadhesive to prevent movement. In some implementations, permanent affixation of the laser fiber or embedding the laser fiber within the hollow needle precisely may be achieved, as illustrated in FIGS. 9-11. The affixation may be achieved using industrial standard bioadhesives. Many types of which are available, including, e.g., the DYMAX 136-M used in the manufacture of medical devices.

Figure 12:
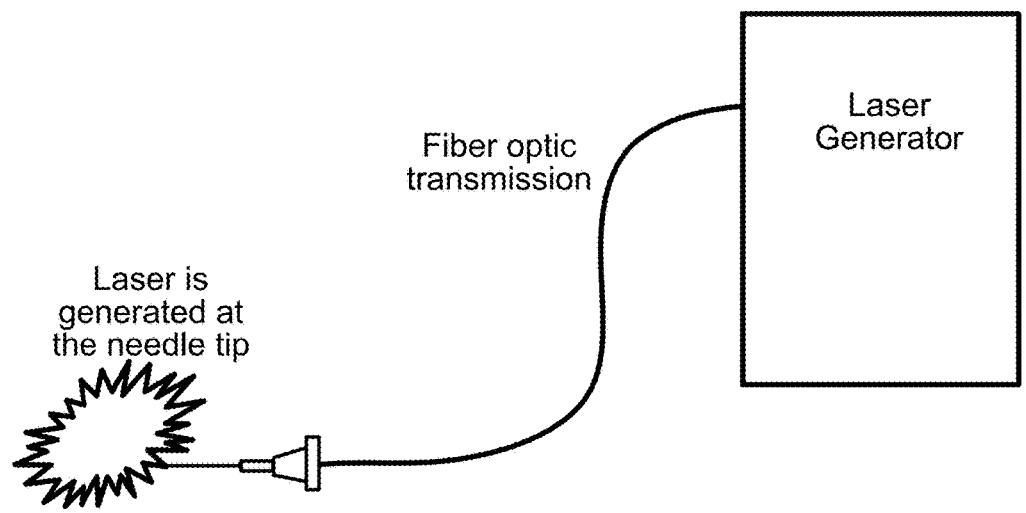
FIG. 12 is a schematic diagram of an example apparatus for delivery of laser energy using the needle.

In FIG. 12, the schematic presentation of the delivery system for use with the needle as discussed above is shown. The delivery system is substantially the same as described in U.S. patent application Ser. No. 12/631,835, entitled, "Method for Deep Tissue Low intensity Therapy For Selective Destruction of Nociceptive (pain) Nerves," which is incorporated herein by reference. However, the presentation in FIG. 12 has no Luer lock mechanism and the fiberoptic transmission is present as one continuous unit along with the needle, the tip of which represents the point of final laser delivery.

Figure 13:
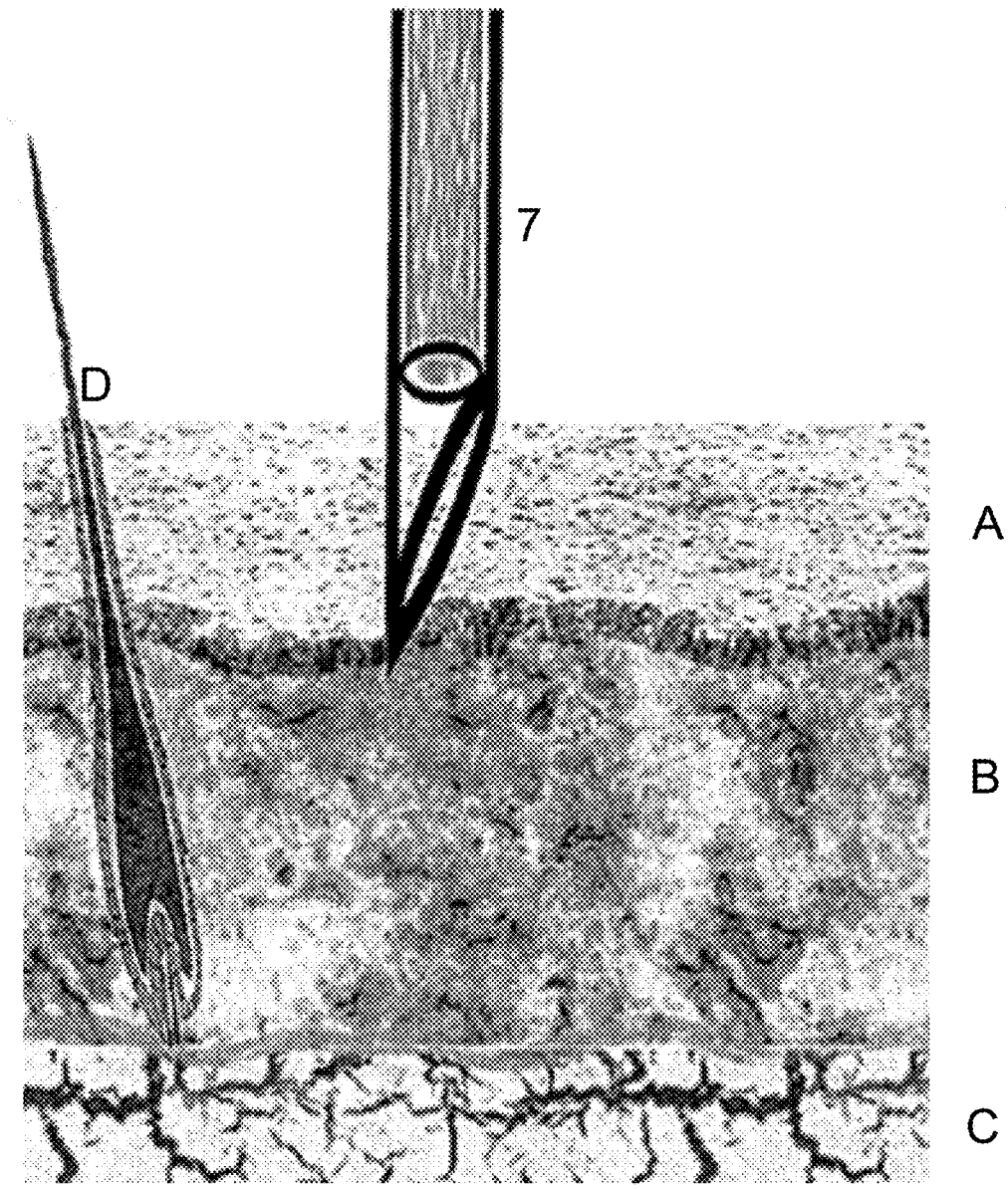
FIG. 13 is a diagram showing the example needle in accordance with embodiments of the present invention entering the skin during use.

FIG. 13 represents the laser fiber embedded hollow needle 7 as the needle penetrates the skin which is represented schematically in cross section (A is epidermis, B is dermis, C is adipose tissue and D is hair arising from a hair follicle). The advantages of the disclosed embodiment are well demonstrated in this figure. As can be seen from the figure, the sharp edge or the cutting edge of the needle can easily penetrate the skin, while the fiber embedded at the cutting edge is clear of the cutting edge and freely passes through the skin without obstructing penetration.

The above-described apparatus facilitates the precise and safe percutaneous delivery of laser energy at the area of treatment, while deeper application is also facilitated by advancing the needle as far as it is needed. As indicated in U.S. patent application Ser. No. 12/631,835, entitled, "Method for Deep Tissue Low intensity Therapy For Selective Destruction of Nociceptive (pain) Nerves," use of this laser embedded needle is facilitated by clinical diagnoses and with the help of image guidance such as X-rays to precisely place the needle at the area of treatment.

A treatment protocol employing the above described laser delivery device, which includes a single needle with a laser fiber affixed to the needle, may include moving the laser delivery device to apply treatments to one spot at a time. Over time, various spots in an area may be treated. Treatment protocols utilizing a needle device for percutaneous delivery may include a longer treatment time, than some implementations disclosed herein. Indeed, some implementations disclosed herein may shorten the treatment time or reduce the number of percutaneous treatments in the context of treating a larger area.

Figure 14A:
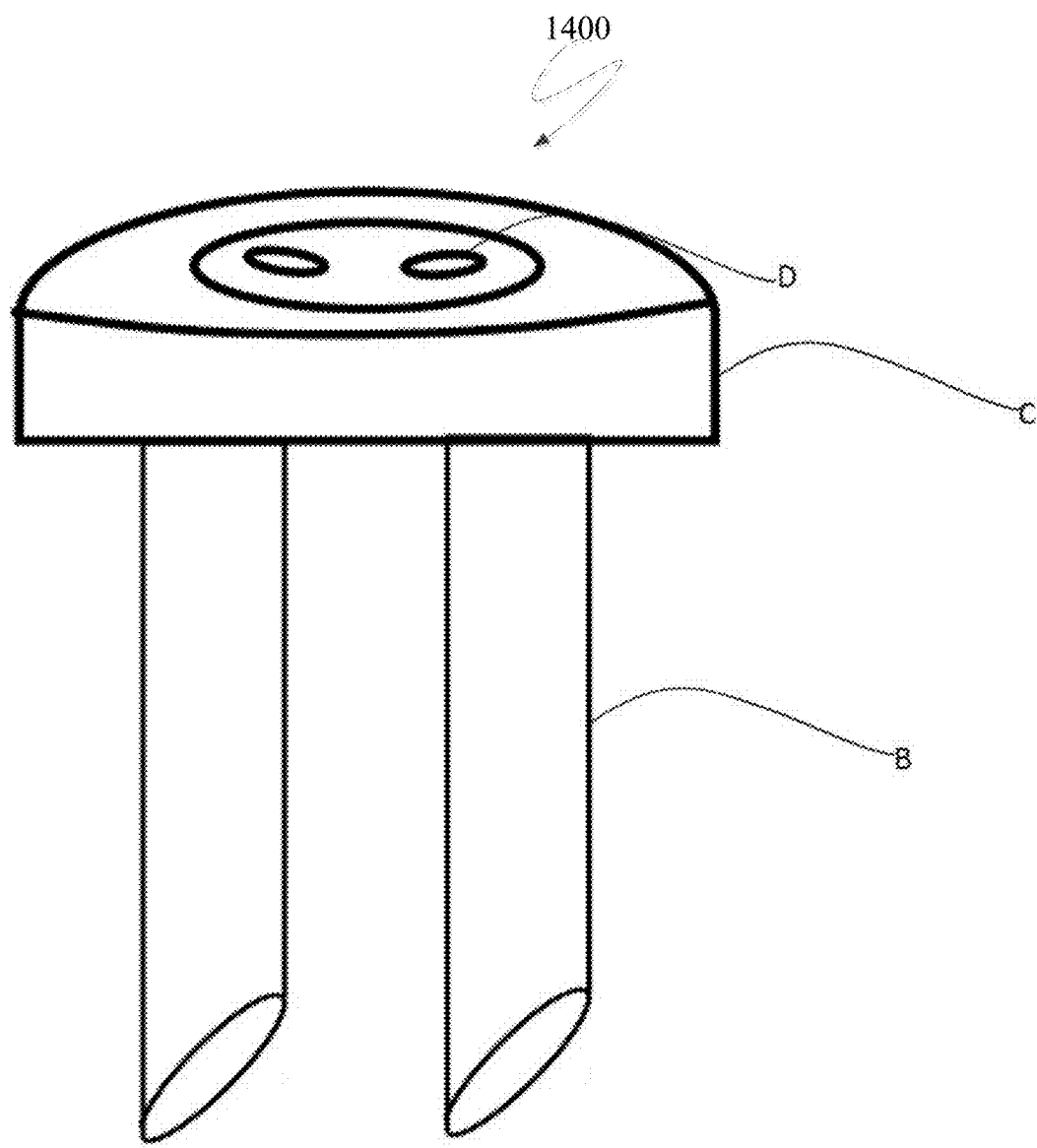
FIG. 14A illustrates an example apparatus for delivery of laser energy using two spikes according to some implementations.

FIG. 14A illustrates an example apparatus 1400 for delivery of laser energy using two spikes according to some implementations. As illustrated, the apparatus 1400 includes two spikes with beveled edges, each of which is indicated by the label B. Each spike B may house an optical fiber capable of transmitting laser energy. In some implementations, each spike may be similar to the needle described in the preceding sections.

Each spike B may be made from steel or some other suitable material. Each spike may be from about 0.5 to about 0.7 mm in diameter and from about 0.5 inch to about 6 inches in length. In some implementations, each adjacent spike may be spaced at no more than 1 cm apart for effective laser delivery. This may be because each point of application of laser can provide an area of effective coverage of about 1 cm in diameter where the physiological effects of pain relief may be related to the area of treatment. The spikes may be placed in a linear fashion, a recti-linear fashion, a circular fashion, or a spiral fashion, to cover a treatment area.

The spikes converge at a hub, labeled as C in FIG. 14. The hub for spike may be plastic, or metal. A connector D may be placed at the distal end of the hub, as shown in FIG. 14. In some implementations, the connector D may be a female SMA 905 adapter socket. The connector D may couple the laser fiber in each spike to a laser source.

Figure 14B:
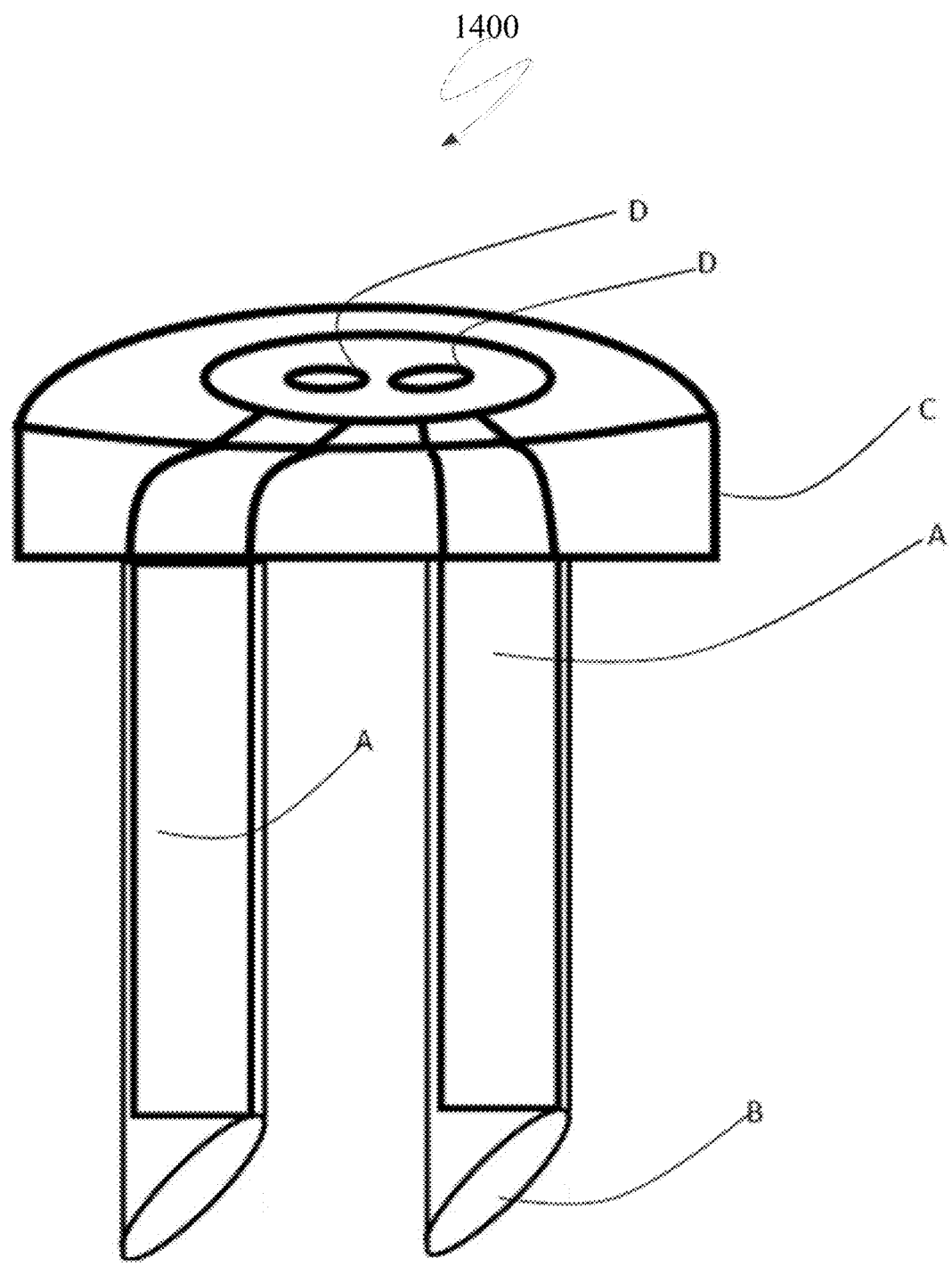
FIG. 14B illustrates the example apparatus for delivery of laser energy using two spikes according to some implementations.

FIG. 14B shows the apparatus 1400 in which each spike B houses an optical fiber A for delivery of laser. The optical fiber A may include a multi-mode fiber. The multi-mode fiber may deliver lasers with laser wavelength in between 440 nm and 980 nm. In some implementations, the preferred wavelength may be in the range of about 690 nm to about 710 nm. In some other implementations, the preferred wavelength may be in the range of about 705 nm to about 710 nm.

The laser delivery may include a pulsed delivery. The laser delivery may be pulsed at, for example, nanoseconds or picoseconds. The laser system may generate an average output power in the range between about 1 mW and about 6 mW. The laser treatment protocol may be timer controlled. In some configurations, the duration of the timer may range between about 5 seconds and about 10 seconds.

Figure 15A:
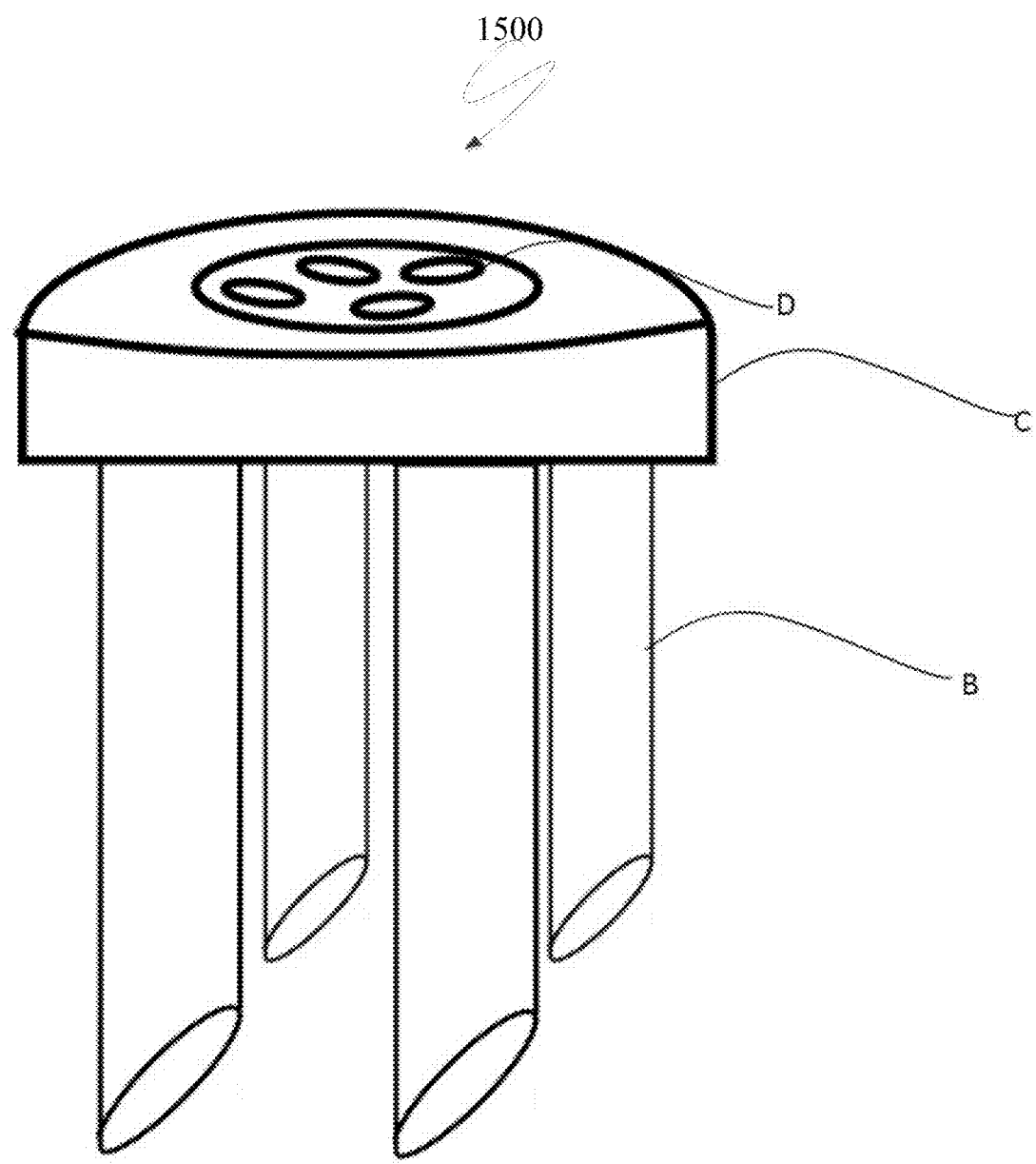
FIG. 15A illustrates another example apparatus for delivery of laser energy using four spikes according to some implementations.

Referring to FIG. 15A, an example apparatus 1500 for delivery of laser energy using four spikes is illustrated. As illustrated, the apparatus 1500 includes four spikes B with beveled edges. Each spike B may house an optical fiber capable of transmitting laser energy. In some implementations, each spike may be similar to the needle described in the preceding sections.

Each spike may be made from some suitable material, e.g., steel. Each spike may be from about 0.5 to about 0.7 mm in diameter and from about 0.5 inch to about 6 inches in length. In some implementations, each adjacent spike may be spaced at no more than 1 cm apart for effective laser delivery, as described previously. The spikes may be placed in a linear fashion, a recti-linear fashion, a circular fashion, or a spiral fashion, to cover a treatment area.

The spikes converge at the hub C. The hub for spike may be plastic, or metal. A connector D may be placed at the distal end of the hub. In some implementations, the connector D may be a female SMA 905 adapter socket. The connector D may couple the laser fiber in each spike to a laser source.

Figure 15B:
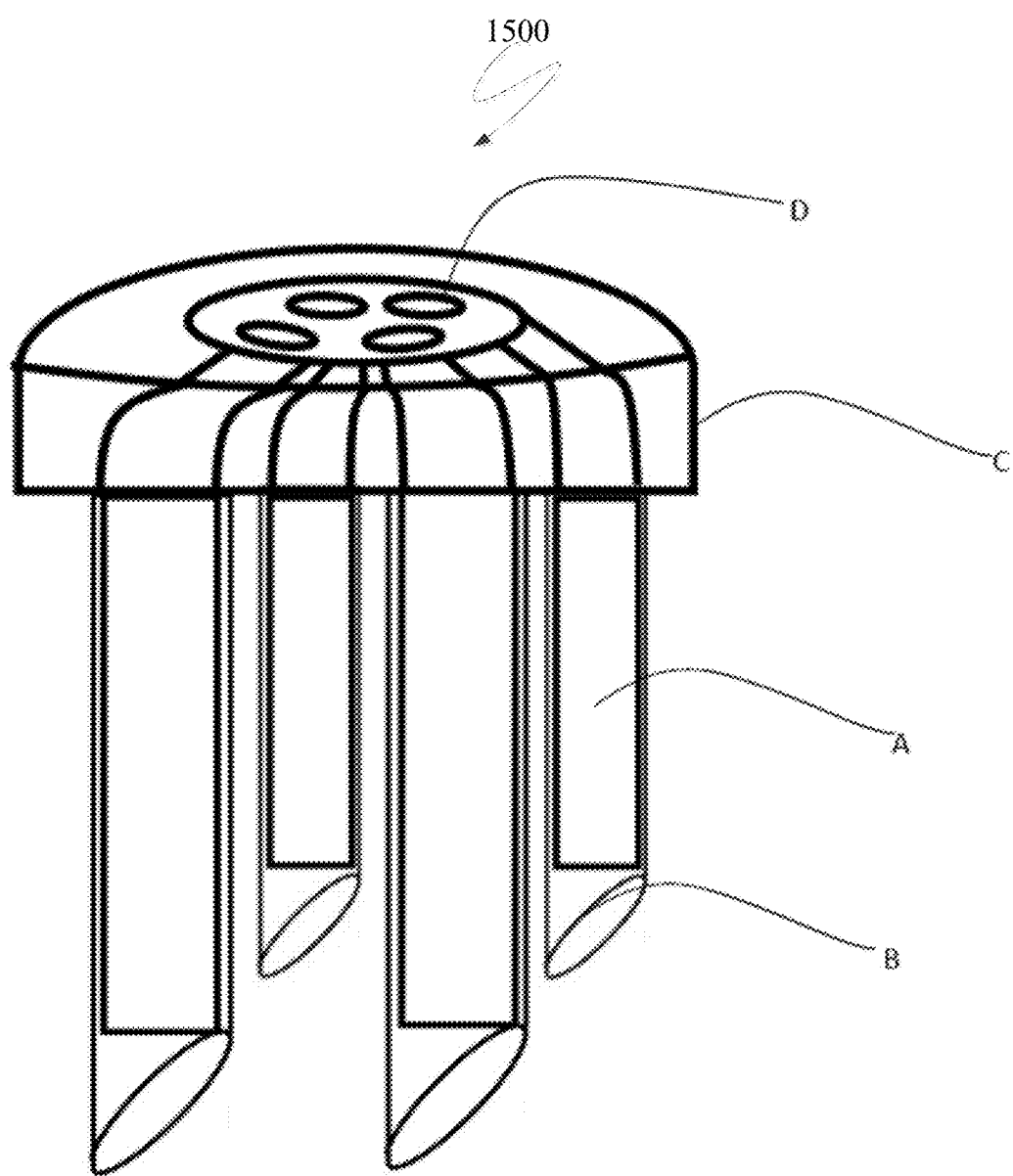
FIG. 15B illustrates the same example apparatus for delivery of laser energy using four spikes according to some implementations.

FIG. 15B illustrates the apparatus 1500 in which each of the four spikes B houses an optical fiber A. In a manner similar to that described above, laser may be delivered through the optical fibers A. The physical dimensions of each optical fiber A are similar to those described above.

Figure 16:
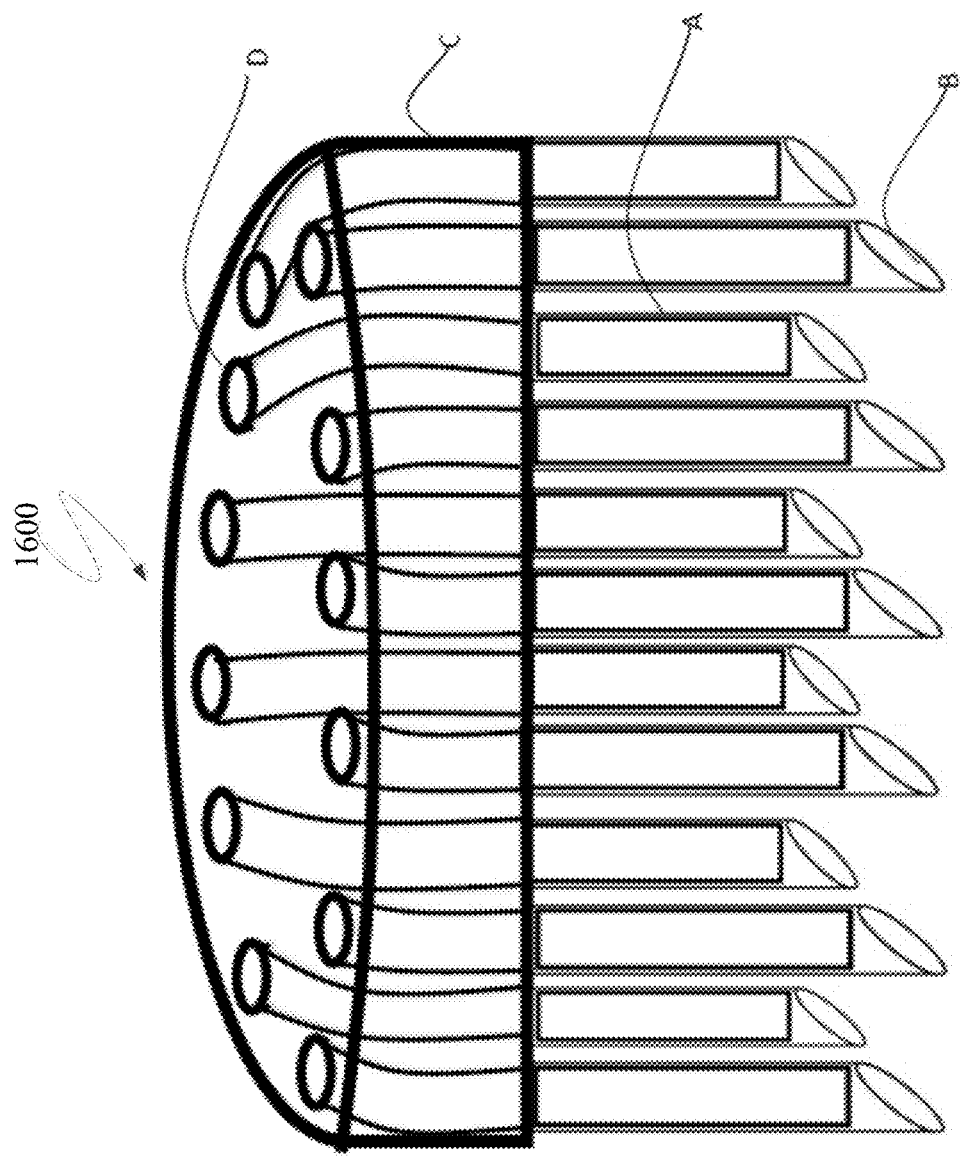
FIG. 16 illustrates an example apparatus for delivery of laser energy using more than four spikes according to some implementations

FIG. 16 illustrates an example apparatus 1600 for delivery of laser energy using more than four spikes according to some implementations. The spikes B, the hub C, the connector D and the optical fibers A included in the apparatus 1600 are similar to the spikes B, hub C, connector D and optical fibers A described with respect to the apparatus 1400 or the apparatus 1500. The apparatus 1600 may be used to treat a larger area with the plurality of spikes B that are mounted using the hub C.

Figure 17:
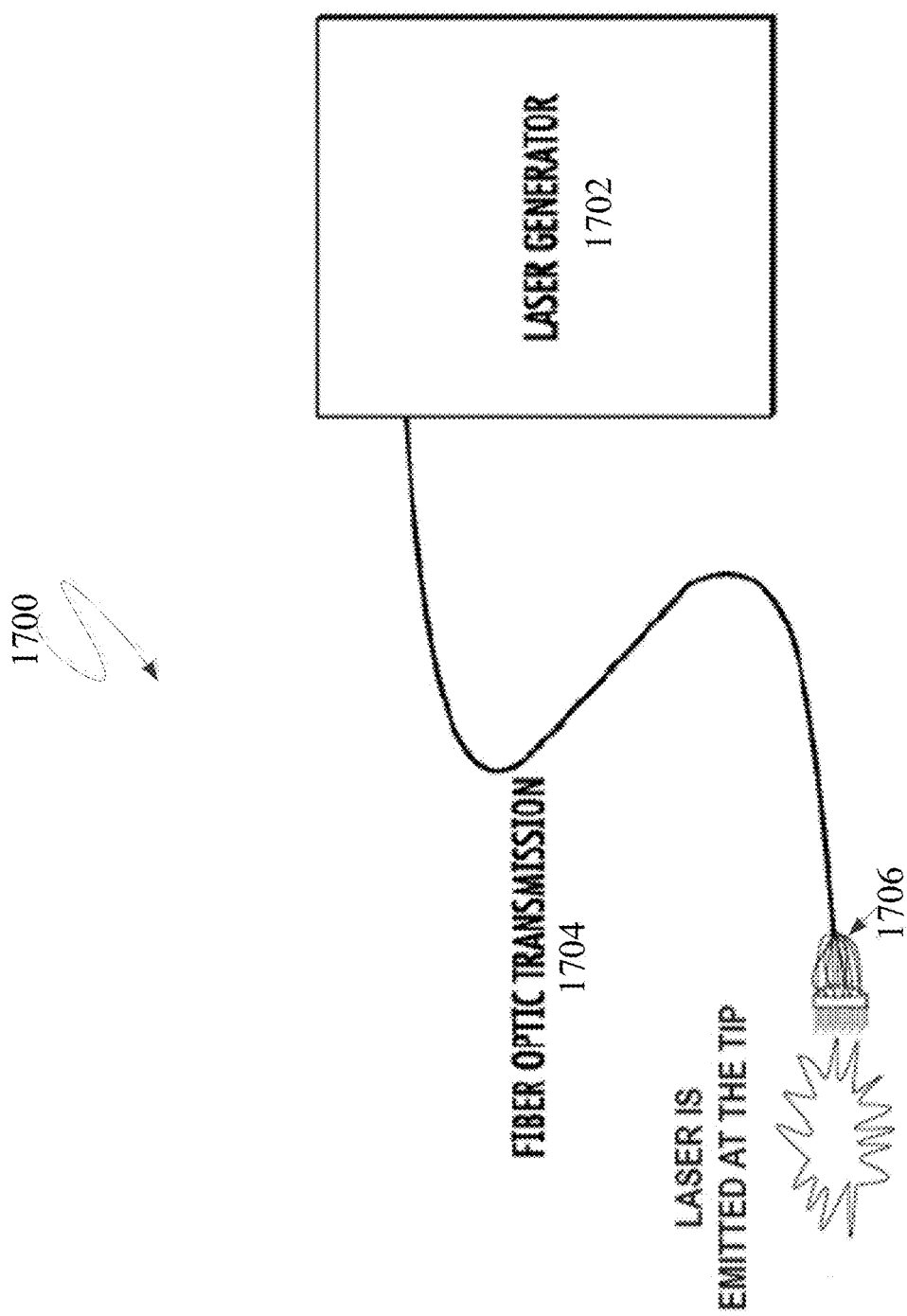
FIG. 17 illustrates an example laser delivery system incorporating multiple spikes according to some implementations.

FIG. 17 illustrates an example laser delivery system 1700 incorporating multiple spikes according to some implementations. The laser generator 1702 may include a highly pulsed low power laser pulsed at nanoseconds or higher. The fiber optic transmission 1704 may utilize a multi-mode fiber to deliver a pulsed laser to the tip of the spikes 1706, such as apparatus 1400, 1500, or 1600. Once emitted, the laser energy may cause cell resonance within the nerve cell can selectively cause destruction of the nerve cells without affecting the surrounding tissues.

Figure 18:
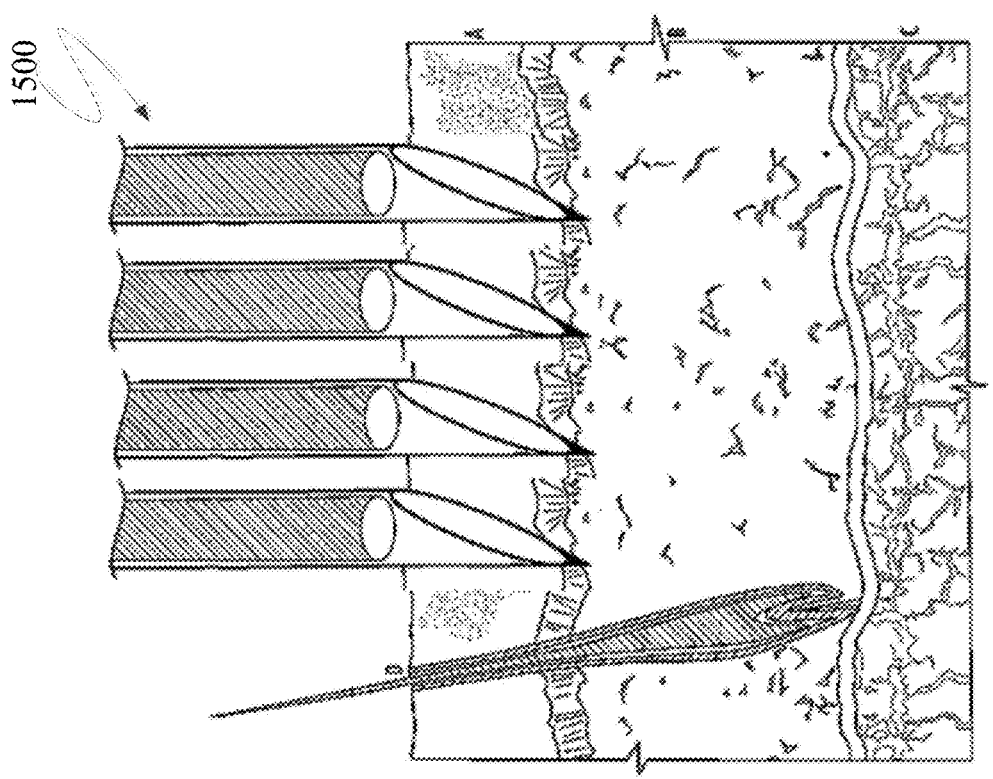
FIG. 18 illustrates percutaneous entry of four laser delivery spikes according to some implementations.

FIG. 18 illustrates percutaneous entry of four laser delivery spikes B according to some implementations. In some implementations, the apparatus 1500 may be used for the laser delivery in FIG. 18. As illustrated, the four spikes B may make simultaneous entries through the skin to deliver laser energy in accordance with the descriptions herein. As discussed herein, treatment protocols utilizing the multi-spike delivery system may expand treatment areas without having to extend treatment time or having to make multiple percutaneous entries in serial.

Figure 19:
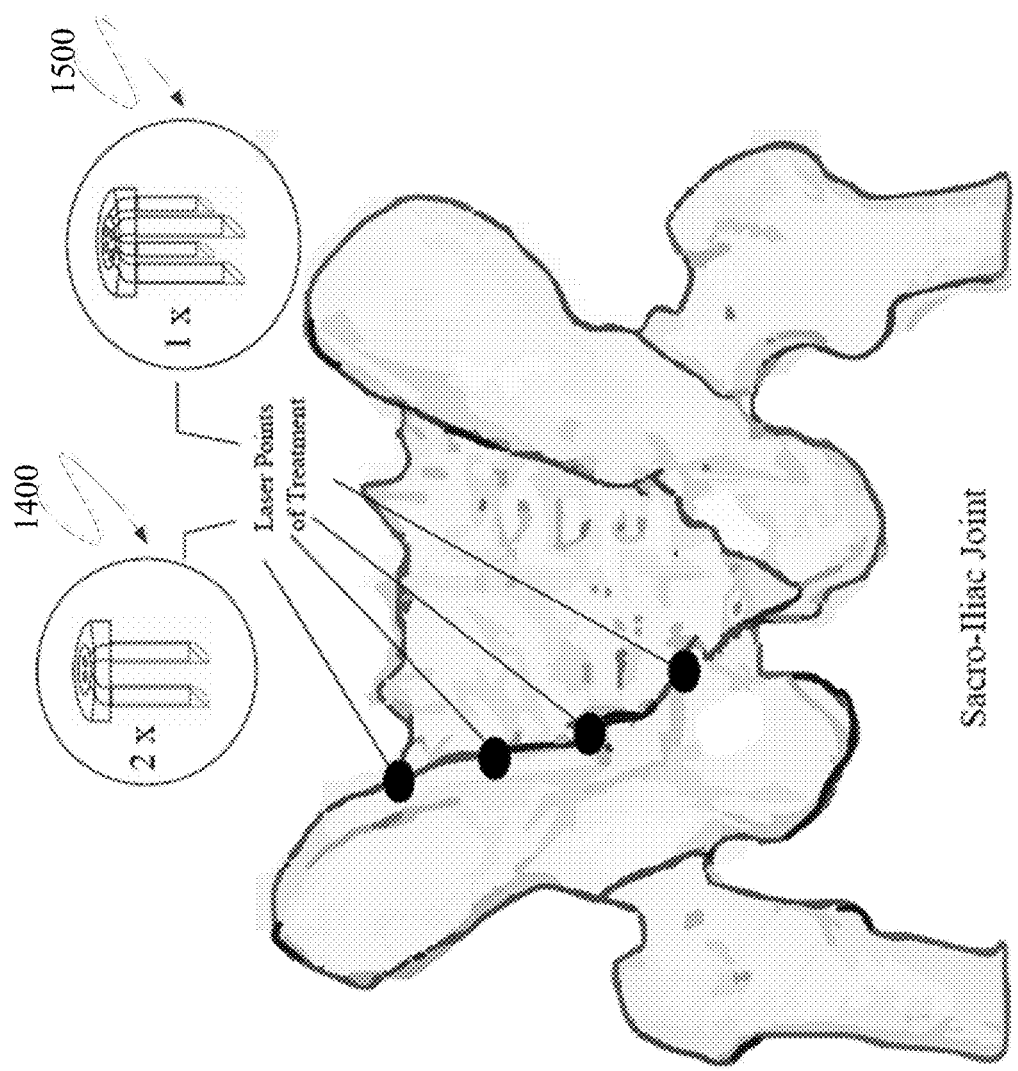
FIG. 19 shows points of laser treatment in an adult sacro-illac (SI) joint according to some implementations.

FIG. 19 shows points of laser treatment in an adult sacro-iliac (SI) joint according to some implementations. The SI joint is a common area of frequent pain symptoms causing back or hip pain. The SI joint is approximately 6-8 cm in length. As illustrated in the posterior view of the SI joint, four laser treatment points are separated by 1-2 cm apart. The laser treatment points may be marked using fluoroscopy, ultrasound or other types of imaging (e.g. X-Ray). Effective laser treatment of the affected SI joint may be achieved by using the apparatus 1400 with the two spikes that would be inserted twice percutaneously. Similar laser treatment may be achieved by using an apparatus similar to the apparatus 1500, but that has four spikes B arranged in a linear fashion which needs to be inserted only once percutaneously but providing a treatment area coverage of two of apparatus 1400 or a single apparatus 1400 that needs to inserted twice as mentioned before.

Example treatment protocols using the disclosed spikes apparatus may apply laser energy to treat a joint area faster than those using the needle apparatus. Specifically, the disclosed spikes apparatus may used at multiple laser points at one time, rather than one laser point at one time. In some examples, the disclosed spikes apparatus may deliver laser at multiple laser points in parallel, thereby reducing treatment time.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

A number of implementations have been described. Nevertheless, it will be understood that various modifications may be made without departing from the spirit and scope of the disclosure. For example, much of this document has been described with respect to messaging and mapping applications, but other forms of graphical applications may also be addressed, such as interactive program guides, web page navigation and zooming, and other such applications.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. An apparatus for percutaneous delivery of laser energy, the apparatus comprising:
    two or more hollow spikes, each having a central cavity, an insertion end, and a coupling end, each including an optical fiber embedded as a permanent fixture in a respective central cavity, each optical fiber capable of emitting laser from the insertion end of the corresponding hollow spike; and
    a hub coupled to the two or more hollow spikes at the respective coupling ends of each hollow spike, the hub including a connector for coupling the apparatus to a laser generator,
    wherein the insertion end of each hollow spike comprises a cutting edge of a Quincke type spinal needle tip, the cutting edge including a beveled edge, and
    wherein each optical fiber is coaxial with an axis of the respective central cavity, and is positioned such that a distal end of the optical fiber is retracted within the respective central cavity corresponding to a plane that is inclined with respect to the axis of the respective central cavity, the plane defining a beginning end of the beveled edge and a distal end of the beveled edge.

2. The apparatus according to claim 1, wherein the embedded optical fiber is permanently fixed within the respective spike with glue.

3. The apparatus according to claim 2, wherein the glue includes a bioadhesive.

4. The apparatus according to claim 1, wherein the respective spike has an outer diameter of 0.7 mm or less.

5. The apparatus according to claim 1, wherein the embedded optical fiber is affixed within the insertion end of the respective spike to deliver the laser energy to an area of treatment on contact with the cutting edge, and wherein the embedded optical fiber is affixed within the insertion end to prevent splitting and damage to the optical fiber.

6. The apparatus according to claim 1, wherein the laser generator is configured to generate a laser of a wavelength in the 690 nm to 710 nm range.

7. The apparatus according to claim 1, wherein the respective optical fiber has a diameter that is less than one of 0.7 mm or 0.5 mm.

8. The apparatus according to claim 1, wherein each hollow spike is spaced no more than 1 cm away from at least one neighboring spike.

9. The apparatus according to claim 1, wherein the respective optical fiber includes a multi-mode fiber.

10. The apparatus according to claim 1, wherein each hollow spike is a Quincke type spinal needle.

11. The apparatus according to claim 1, further comprising: an imaging device to track the insertion ends of the two or more hollow spikes.

12. The apparatus according to claim 11, wherein the imaging device comprises an X-Ray fluoroscopy device.

13. The apparatus according to claim 11, wherein the imaging device comprises: an ultrasound device.

14. The apparatus according to claim 1, further comprising: a motor connected to the hub, the motor configured to cause the percutaneous delivery of laser energy to change position inside a treatment area.

15. A method of percutaneous application of laser energy for medical treatment, the method comprising:
    coupling a laser generator to a hub that is connected to two or more hollow spikes, wherein a connector included in the hub is configured to couple the laser generator to the hub, and wherein each hollow spike includes a central cavity, an insertion end, a coupling end that is connected to the hub, and an optical fiber that is embedded in a respective central cavity as a permanent fixture;
    percutaneously inserting the insertion ends of the two or more hollow spikes into a treatment area through a subject's skin, wherein the two or more hollow spikes are inserted at a same time; and
    delivering laser energy to the treatment area through the optical fibers housed within the two or more spikes,
    wherein the insertion end of each hollow spike comprises a cutting edge of a Quincke type spinal needle tip, the cutting edge including a beveled edge, and
    wherein each optical fiber is coaxial with an axis of the respective central cavity, and is positioned such that a distal end of the optical fiber is retracted within the respective central cavity corresponding to a plane that is inclined with respect to the axis of the respective central cavity, the plane defining a beginning end of the beveled edge and a distal end of the beveled edge.

16. The method of claim 15, wherein percutaneously inserting the beveled edges further comprises:
    percutaneously inserting the beveled edges under imaging guidance.

17. The method of claim 15, wherein delivering the laser energy further comprises:
    targeting laser energy within the treatment area under imaging guidance.

* * * * *